United States Patent
Metcalf

(10) Patent No.: US 11,576,413 B2
(45) Date of Patent: Feb. 14, 2023

(54) COMPOSITIONS COMPRISING IONIZED CANNABIDIOL

(71) Applicant: Natural Extraction Systems, LLC, Boulder, CO (US)

(72) Inventor: Douglas G. Metcalf, Erie, CO (US)

(73) Assignee: NATURAL EXTRACTION SYSTEMS, LLC, Boulder, CO (US)

(*) Notice: Subject to any disclaimer, the term of this patent is extended or adjusted under 35 U.S.C. 154(b) by 206 days.

(21) Appl. No.: 16/839,997

(22) Filed: Apr. 3, 2020

(65) Prior Publication Data

US 2020/0315229 A1 Oct. 8, 2020

Related U.S. Application Data

(63) Continuation of application No. 16/239,463, filed on Jan. 3, 2019, now Pat. No. 10,609,944.

(60) Provisional application No. 62/787,717, filed on Jan. 2, 2019, provisional application No. 62/780,169, filed on Dec. 14, 2018.

(51) Int. Cl.
| | |
|---|---|
| *A23L 33/105* | (2016.01) |
| *A23L 2/52* | (2006.01) |
| *A61K 36/185* | (2006.01) |
| *A23L 29/00* | (2016.01) |

(52) U.S. Cl.
CPC ........... *A23L 33/105* (2016.08); *A23L 2/52* (2013.01); *A23L 29/035* (2016.08); *A61K 36/185* (2013.01); *A23V 2002/00* (2013.01); *A23V 2250/2132* (2013.01)

(58) Field of Classification Search
None
See application file for complete search history.

(56) References Cited

U.S. PATENT DOCUMENTS

| | | |
|---|---|---|
| 9,907,823 B1 | 3/2018 | Kuhrts |
| 10,555,914 B1 | 2/2020 | Metcalf |
| 10,609,944 B1 | 4/2020 | Metcalf |
| 2007/0105086 A1 | 5/2007 | Qin |
| 2009/0044700 A1 | 2/2009 | Dietlin |
| 2014/0263467 A1 | 9/2014 | Wardle |
| 2016/0018424 A1 | 1/2016 | Lucas |
| 2017/0246897 A1 | 8/2017 | Brehm |
| 2018/0169035 A1 | 6/2018 | Eyal |
| 2019/0030170 A1 | 1/2019 | Kingsley |

FOREIGN PATENT DOCUMENTS

| | | |
|---|---|---|
| CN | 108314608 A | 7/2018 |
| EP | 3061450 A1 | 8/2016 |
| EP | 3459536 A1 | 3/2019 |
| WO | 2006133941 A2 | 12/2006 |
| WO | 2018183115 A1 | 10/2018 |

OTHER PUBLICATIONS

U.S. Appl. No. 17/311,971 filed Jun. 2021, Metcalf, Douglas.*
Dow Corning, "Corning® Plastic Storage Bottles Selection Guide," 2016, 8 pages.
Gelderblom et al., "Cremophor EL: the drawbacks and advantages of vehicle selection for drug formulation," European Journal of Cancer, 2001, pp. 1590-1998, vol. 37.
Kogan et al., "Synthesis and antitumor activity of quinonoid derivatives of cannabinoids," Journal of Medicinal Chemistry, 2004, pp. 3800-3806, vol. 47, issue 15.
Layton et al., "Forced degradation of cannabidiol," 2016, publisher Waters Corporation, 6 pages.
Martijn, "CBD products according to sensi seeds," 2016, 12 pages.
Mazina et al., "A rapid capillary electrophoresis method with LED-induced native fluorescence detection for the analysis of cannabinoids in oral fluid," Analytical Methods, 2015, pp. 7741-7747, vol. 7.
Mechoulam et al., "Hashish-X111: On the nature of the beam test," Tetrahedron, 1968, pp. 5615-5624, vol. 24, issue 16.
Mechoulam et al., "Cannabidiol: an overview of some chemical and pharmacological aspects. Part I: chemical aspects," Chemistry and Physics of Lipids, 2002, pp. 35-43, vol. 121.
Srebnik et al., "Base-catalysed double-bond isomerizations of cannabinoids: structural and stereochemical aspects," Journal of the Chemical Society, Perkin Transactions I, 1984, pp. 2881-2886.
Wilson et al., "HU-331 and oxidized cannabidiol acts as inhibitors of human topoisomerase IIα and β," Chemical Research in Toxicology, 2017, pp. 137-144, vol. 31.

* cited by examiner

*Primary Examiner* — Michael Barker
(74) *Attorney, Agent, or Firm* — Holland & Hart LLP

(57) ABSTRACT

Various aspects of the disclosure relate to compositions comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol.

20 Claims, No Drawings

COMPOSITIONS COMPRISING IONIZED CANNABIDIOL

CROSS-REFERENCE TO RELATED APPLICATIONS

This patent document claims priority to U.S. Provisional Patent Application No. 62/780,169, filed Dec. 14, 2018; U.S. Provisional Patent Application No. 62/787,717, filed Jan. 2, 2019; and U.S. patent application Ser. No. 16/239,463, filed Jan. 3, 2019, which granted as U.S. Pat. No. 10,609,944, and each of the preceding applications is incorporated by reference in its entirety.

BACKGROUND

The *Cannabis* plant produces cannabidiolic acid, which displays only nominal pharmacological activity. Cannabidiolic acid can be converted into cannabidiol, which displays robust pharmacological activity, by heating cannabidiolic acid under vacuum.

Cannabidiol is sparingly soluble in water. Attempts have been made to improve the solubility of cannabidiol to produce beverages suitable for human consumption, for example, by emulsification. Thermostable emulsions of cannabidiol frequently display unfavorable characteristics including undesirable flavor. Improved methods of solubilizing cannabidiol are desirable to produce beverages comprising cannabidiol.

BRIEF DESCRIPTION

Various aspects of this patent document relate to a composition, comprising: 2-[(1R,6R)-6-isopropenyl-3-methylcyclohex-2-en-1-yl]-3-hydroxy-5-pentylphenolate; 2-[(1R,6R)-6-isopropenyl-3-methylcyclohex-2-en-1-yl]-5-pentylbenzene-1,3-diol; water; and potassium ion ($K^+$), wherein: the composition is a liquid; and the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:10 and no greater than 1,000,000:1.

In some embodiments, the composition comprises the 2-[(1R,6R)-6-isopropenyl-3-methylcyclohex-2-en-1-yl]-3-hydroxy-5-pentylphenolate at a concentration by weight of at least 5 percent and no greater than 25 percent.

In some embodiments, the composition comprises ethanol at a concentration by weight of at least 10 percent and no greater than 95 percent.

In some embodiments, the composition comprises the water at a concentration by weight of at least 1 percent and no greater than 10 percent.

In some embodiments, the composition comprises the potassium ion at a concentration of at least 10 millimoles per liter and no greater than 1 mole per liter.

In some embodiments, the composition comprises the 2-[(1R,6R)-6-isopropenyl-3-methylcyclohex-2-en-1-yl]-3-hydroxy-5-pentylphenolate at a concentration by weight of at least 5 parts per million and no greater than 10 percent.

In some embodiments, the composition comprises ethanol at a concentration by weight of at least 10 percent by and no greater than 95 percent.

In some embodiments, the composition comprises ethanol at a concentration by weight of at least 1 percent and no greater than 20 percent.

In some embodiments, the composition comprises ethanol at a concentration by weight of at least 10 parts per trillion and no greater than 0.5 percent.

In some embodiments, the composition comprises the water at a concentration by weight of at least 50 percent and no greater than 99.999 percent, wherein the 2-[(1R,6R)-6-isopropenyl-3-methylcyclohex-2-en-1-yl]-3-hydroxy-5-pentylphenolate is dissolved in the water.

In some embodiments, the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:1 and no greater than 10,000:1.

In some embodiments, the composition has a pH of at least 8 and no greater than 12.

In some embodiments, the composition comprises one or more of sulfate ($SO_4^{2-}$), carbonate ($CO_3^{2-}$), bicarbonate ($HCO_3^{1-}$), phosphate ($PO_4^{3-}$), hydrogen phosphate ($HPO_4^{2-}$), hydrogen pyrophosphate ($HP_2O_7^{3-}$), hydrogen triphosphate ($HP_3O_{10}^{4-}$), and triphosphate ($P_3O_{10}^{5-}$).

In some embodiments, the composition comprises sodium ion ($Na^+$), wherein the composition comprises the potassium ion and the sodium ion at a combined concentration of at least 10 milligrams per liter and no greater than 1000 milligrams per liter.

In some embodiments, the composition comprises chloride ion ($Cl^{1-}$).

In some embodiments, the composition comprises calcium ion ($Ca^{2+}$).

In some embodiments, the composition comprises one or more of adenosylcobalamin, ascorbate, biotin, cyanocobalamin, folate, hydroxocobalamin, methylcobalamin, niacin, nicotinamide, pantothenate, pyridoxal, pyridoxamine, pyridoxine, riboflavin, thiamin, caffeine, theobromine, sucrose, fructose, glucose, acesulfame, saccharin, stevioside, rebaudioside A, sucralose, tagatose, erythritol, maltitol, xylitol, mannitol, isomalt, and a mogroside. In some specific embodiments, the composition comprises at least 5 milligrams and no greater than 500 milligrams of caffeine.

Various aspects of this patent document relate to a liquid composition, comprising: 2-[(1R,6R)-6-isopropenyl-3-methylcyclohex-2-en-1-yl]-3-hydroxy-5-pentylphenolate at a concentration by weight of at least 5 percent and no greater than 25 percent; 2-[(1R,6R)-6-isopropenyl-3-methylcyclohex-2-en-1-yl]-5-pentylbenzene-1,3-diol, wherein the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:10 and no greater than 1,000,000:1; ethanol at a concentration by weight of at least 10 percent and no greater than 95 percent; water at a concentration by weight of at least 1 percent and no greater than 10 percent; and potassium ion ($K^+$) at a concentration of at least 10 millimoles per liter and no greater than 1 mole per liter.

Various aspects of this patent document relate to a liquid composition, comprising: 2-[(1R,6R)-6-isopropenyl-3-methylcyclohex-2-en-1-yl]-3-hydroxy-5-pentylphenolate at a concentration by weight of at least 5 parts per million and no greater than 10 percent; 2-[(1R,6R)-6-isopropenyl-3-methylcyclohex-2-en-1-yl]-5-pentylbenzene-1,3-diol, wherein the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:1 and no greater than 10,000:1; water; ethanol; and potassium ion ($K^+$) and sodium ion ($Na^+$) at a combined concentration of at least 10 milligrams per liter and no greater than 1000 milligrams per liter.

DETAILED DESCRIPTION

Various aspects of the disclosure relate to the discovery that 2-[(1R,6R)-6-isopropenyl-3-methylcyclohex-2-en-1-yl]-3-hydroxy-5-pentylphenolate is stable in water at a pH of less than 9.5. This discovery was unexpected and surprising because the $pK_a$ of 2-[(1R,6R)-6-isopropenyl-3-methylcyclohex-2-en-1-yl]-5-pentylbenzene-1,3-diol (cannabidiol; "1R,6R CBD"), which is the conjugate acid of 2-[(1R,6R)-6-isopropenyl-3-methylcyclohex-2-en-1-yl]-3-hydroxy-5-pentylphenolate, was previously determined to be greater than 9 and also because 1R,6R CBD lacks appreciable solubility in water. Based on this information, the beverage and nutritional supplement industries overlooked attempts to solubilize 1R,6R CBD under alkaline conditions. The present disclosure reveals that 2-[(1R,6R)-6-isopropenyl-3-methylcyclohex-2-en-1-yl]-3-hydroxy-5-pentylphenolate is soluble and stable in water at pH ranges below 10. The ramifications of this discovery include the development of commercially-viable beverages that comprise 2-[(1R,6R)-6-isopropenyl-3-methylcyclohex-2-en-1-yl]-3-hydroxy-5-pentylphenolate.

Various aspects of the disclosure relate to 2-[(1R,6R)-6-isopropenyl-3-methylcyclohex-2-en-1-yl]-3-hydroxy-5-pentylphenolate and compositions comprising 2-[(1R,6R)-6-isopropenyl-3-methylcyclohex-2-en-1-yl]-3-hydroxy-5-pentylphenolate.

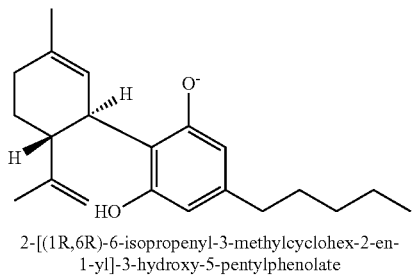 [SMILES: C=C(C)[C@@H]1CCC(C)=C[C@H]1c1c([O-])cc(CCCCC)cc1O]

2-[(1R,6R)-6-isopropenyl-3-methylcyclohex-2-en-1-yl]-3-hydroxy-5-pentylphenolate In some embodiments, a composition comprises a salt of 2-[(1R,6R)-6-isopropenyl-3-methylcyclohex-2-en-1-yl]-3-hydroxy-5-pentylphenolate. The salt can be, for example, a sodium salt, potassium salt, calcium salt, or magnesium salt.

In some embodiments, a composition comprises 1R,6R CBD.

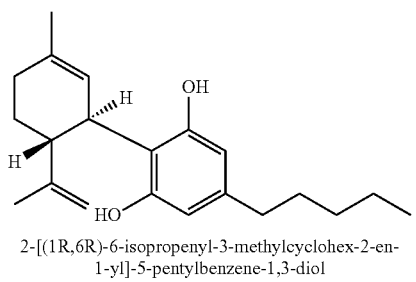 [SMILES: C=C(C)[C@@H]1CCC(C)=C[C@H]1c1c(O)cc(CCCCC)cc1O]

2-[(1R,6R)-6-isopropenyl-3-methylcyclohex-2-en-1-yl]-5-pentylbenzene-1,3-diol

In some embodiments, a composition lacks chlorophyll, cellulose, or both chlorophyll and cellulose.

In some embodiments, a composition comprises 2-[(1R,6R)-6-isopropenyl-3-methylcyclohex-2-en-1-yl]-3-hydroxy-5-pentylphenolate at a concentration of 5 parts per million ("ppm") to 10% by weight. In some embodiments, a composition comprises 2-[(1R,6R)-6-isopropenyl-3-methylcyclohex-2-en-1-yl]-3-hydroxy-5-pentylphenolate at a concentration of 5% to 97% by weight.

In some embodiments, a composition further comprises water, ethanol, or both water and ethanol.

In some embodiments, a composition comprises water at a concentration by weight of at least 10%. In some embodiments, a composition comprises water at a concentration by weight of 10% to 99.999%.

In some embodiments, a composition comprises ethanol at a concentration by weight of at least 10 parts per trillion ("ppt") such as at least 10 parts per billion ("ppb"). In some embodiments, a composition comprises ethanol at a concentration by weight of 10 ppt to 0.5%.

In some embodiments, a composition comprises ethanol at a concentration by weight of at least 0.1%. In some embodiments, a composition comprises ethanol at a concentration by weight of 0.1% to 1%, 0.5% to 5%, 1% to 10%, or 5% to 15%.

In some embodiments, a composition comprises ethanol at a concentration by weight of at least 10%. A composition can comprise ethanol at a concentration by weight of 10% to 99.9%.

In some embodiments, a composition comprises sodium ion at a concentration by weight of at least 10 ppb. A composition can optionally comprise sodium ion at a concentration by weight of 10 ppb to 10%.

In some embodiments, a composition comprises potassium ion at a concentration by weight of at least 10 ppb. A composition can optionally comprise potassium ion at a concentration by weight of 10 ppb to 10%.

In some embodiments, a composition comprises sodium ion and potassium ion at a total concentration by weight of at least 10 ppb. A composition can optionally comprise sodium ion and potassium ion at a total concentration by weight of 10 ppb to 10%.

In some embodiments, a composition further comprises sucrose, fructose, glucose, acesulfame, aspartame, saccharin, stevia, sucralose, tagatose, neotame, sorbitol, xylitol, erythritol, maltitol, mannitol, isomalt, or lactitol.

In some embodiments, a composition has a pH of 7 to 14, 7 to 12, 8 to 12, 9 to 12, 10 to 12, 11 to 12, 7 to 11, 8 to 11, 9 to 1, 10 to 11, 7 to 9, 8 to 10, 9 to 11, 10 to 12, 11 to 13, 12 to 14, 7 to 8, 7.5 to 8.5, 8 to 9, 8.5 to 9.5, 9 to 10, 9.5 to 10.5, 10 to 11, 10.5 to 11.5, 11 to 12, 11.5 to 12.5, 12 to 13, 12.5 to 13.5, or 13 to 14.

In some embodiments, a composition further comprises carbonate, bicarbonate, or both carbonate and bicarbonate. For example, a composition can comprise carbonate and bicarbonate at a total concentration by weight of at least 10 ppb. A composition can optionally comprise carbonate and bicarbonate at a total concentration by weight of 10 ppb to 10%.

Various aspects of the present disclosure relate to a sealed container comprising a composition described anywhere in the present disclosure. In some embodiments, the sealed container is a glass bottle, aluminum can (which optionally comprises a polymer liner disposed within the aluminum can), or a plastic bottle. A sealed container can be, for example, a barrel, jar, can, bottle, box, pouch, or molded plastic. A sealed container typically comprises a sealed chamber in which a composition according to the present disclosure is disposed.

A sealed container can optionally be sealed with a cap such as a screw cap.

In some embodiments, a container comprises at least 1 milligram ("mg") of a composition described in the present disclosure. In some embodiments, a container comprises 1 mg to 1000 kg of a composition described in the present disclosure.

In some embodiments, a container comprises at least 1 microliter of a composition described in the present disclosure. In some embodiments, a container comprises 1 microliter to 1000 L of a composition described in the present disclosure.

In some embodiments, a composition is suitable for human consumption. In some embodiments, a composition is a beverage.

Numerous combinations of the features described in the present disclosure are possible, and the inventors contemplate each possible combination of features as would be apparent to one of ordinary skill in the relevant arts at the Dec. 14, 2018 priority date of this patent document. The words "comprise," "comprising," and their alternate forms refer to open sets to which additional features can optionally be added. The following exemplification section discloses specific embodiments that fall within the scope of the preceding description, and the examples set forth in the exemplification section do not limit the present disclosure or following claims in any way.

EXEMPLIFICATION

Example 1. Preparation of 2-[(R,6R)-6-isopropenyl-3-methylcyclohex-2-en-1-yl]-3-hydroxy-5-pentylphenolate 0.5 grams of 1R,6R CBD was dissolved in 3.3 milliliters 0.5 molar potassium hydroxide (0.5 M KOH) in ethanol to produce 2-[(1R,6R)-6-isopropenyl-3-methylcyclohex-2-en-1-yl]-3-hydroxy-5-pentylphenolate. The conversion of 1R,6R CBD to 2-[(1R,6R)-6-isopropenyl-3-methylcyclohex-2-en-1-yl]-3-hydroxy-5-pentylphenolate was readily confirmed by color because 1R,6R CBD has a yellow-brown color and 2-[(1R,6R)-6-isopropenyl-3-methylcyclohex-2-en-1-yl]-3-hydroxy-5-pentylphenolate has a deep purple color.

The 2-[(1R,6R)-6-isopropenyl-3-methylcyclohex-2-en-1-yl]-3-hydroxy-5-pentylphenolate was diluted with 26.7 milliliters of 0.1 molar sodium carbonate (0.1 M $Na_2CO_3$) and divided into three aliquots of 10 milliliters each, each aliquot containing approximately:

167 milligrams 2-[(1R,6R)-6-isopropenyl-3-methylcyclohex-2-en-1-yl]-3-hydroxy-5-pentylphenolate
21 milligrams potassium ion
41 milligrams sodium ion
53 milligrams carbonate
868 milligrams ethanol
8.8 grams water Example 2. Preparation of Salts Comprising 2-[(R,6R)-6-isopropenyl-3-methylcyclohex-2-en-1-yl]-3-hydroxy-5-pentylphenolate A first aliquot from Example 1 was lyophilized to produce salts including a potassium 2-[(1R,6R)-6-isopropenyl-3-methylcyclohex-2-en-1-yl]-3-hydroxy-5-pentylphenolate salt and a sodium 2-[(1R,6R)-6-isopropenyl-3-methylcyclohex-2-en-1-yl]-3-hydroxy-5-pentylphenolate salt.

Example 3. Reconstituting 1R,6R CBD 0.1 milliliters of 5 molar citric acid (5 M citric acid) was added to a second aliquot from Example 1 to reconstitute 1R,6R CBD from 2-[(1R,6R)-6-isopropenyl-3-methylcyclohex-2-en-1-yl]-3-hydroxy-5-pentylphenolate. The reconstitution of 1R,6R CBD was confirmed by color.

Example 4. Determining pH Stability of 2-[(R,6R)-6-isopropenyl-3-methylcyclohex-2-en-1-yl]-3-hydroxy-5-pentylphenolate in Water Various acid dissociation constants ($K_a$) for the 1R,6R CBD hydroxyl protons have been reported, and the corresponding $pK_a$'s (which are the negative $\log_{10}$'s of the acid dissociation constants) range from 9.13 to 9.64. This data suggests that 2-[(1R,6R)-6-isopropenyl-3-methylcyclohex-2-en-1-yl]-3-hydroxy-5-pentylphenolate is not viable for inclusion in beverages. If the $pK_a$ of 1R,6R CBD were 9.13, for example, then 1R,6R CBD might be expected to lack stability at a pH of 9.5 because approximately 30% of the dissolved 2-[(1R,6R)-6-isopropenyl-3-methylcyclohex-2-en-1-yl]-3-hydroxy-5-pentylphenolate and 1R,6R CBD would exist as 1R,6R CBD, which might form a lipid phase. This lipid phase would be a thermodynamic sink if the lipid phase were to separate from the aqueous phase. Le Châtelier's principle could drive the conversion of 2-[(1R,6R)-6-isopropenyl-3-methylcyclohex-2-en-1-yl]-3-hydroxy-5-pentylphenolate to 1R,6R CBD until the composition existed as an aqueous phase essentially devoid of 2-[(1R,6R)-6-isopropenyl-3-methylcyclohex-2-en-1-yl]-3-hydroxy-5-pentylphenolate and a lipid phase comprising 1R,6R CBD. A greater $pK_a$, such as a $pK_a$ of 9.64, would magnify this detrimental effect. Beverages having a pH above 9.5 to 10 are uncommon because they risk causticity.

Experiments were nevertheless performed to determine whether 2-[(1R,6R)-6-isopropenyl-3-methylcyclohex-2-en-1-yl]-3-hydroxy-5-pentylphenolate could be stabilized in aqueous solution. 1 gram of 1R,6R CBD was dissolved in 6.6 milliliters of 0.5 molar potassium hydroxide (0.5 M KOH) in ethanol to produce 2-[(1R,6R)-6-isopropenyl-3-methylcyclohex-2-en-1-yl]-3-hydroxy-5-pentylphenolate. The solution was then diluted with 100 millimolar sodium carbonate (100 mM $Na_2CO_3$) in water to a final volume of 50 milliliters and to a 2-[(1R,6R)-6-isopropenyl-3-methylcyclohex-2-en-1-yl]-3-hydroxy-5-pentylphenolate concentration of approximately 20 grams per liter. 0.5 milliliters of the 2-[(1R,6R)-6-isopropenyl-3-methylcyclohex-2-en-1-yl]-3-hydroxy-5-pentylphenolate solution was added to each of 25 test tubes containing 9.5 milliliters of 0.1 molar carbonate/bicarbonate ($CO_3^{2-}/HCO_3^{1-}$) buffer according to Table 1. Each test tube contained approximately 10 milligrams of 2-[(1R,6R)-6-isopropenyl-3-methylcyclohex-2-en-1-yl]-3-hydroxy-5-pentylphenolate at a concentration of approximately 1 gram per liter, approximately 0.66% ethanol by weight, trace potassium ion, and variable sodium ion, carbonate ion, and bicarbonate ion. pH's were confirmed by multiple different measurements.

TABLE 1

Aqueous compositions comprising 2-[(1R,6R]-6-isopropenyl-3-methylcyclohex-2-en-1-yl]-3-hydroxy-5-pentylphenolate at variable pH

| Sample | pH | 0.1M $Na_2CO_3$* | 0.1M $NaHCO_3$ |
| --- | --- | --- | --- |
| 1 | 9.1 | 0.06 mL | 8.94 mL |
| 2 | 9.2 | 0.20 mL | 8.80 mL |
| 3 | 9.3 | 0.36 mL | 8.64 mL |

TABLE 1-continued

Aqueous compositions comprising
2-[(1R,6R]-6-isopropenyl-3-methylcyclohex-2-en-1-yl]-3-
hydroxy-5-pentylphenolate at variable pH

| Sample | pH | 0.1M Na$_2$CO$_3$* | 0.1M NaHCO$_3$ |
|---|---|---|---|
| 4 | 9.4 | 0.56 mL | 8.44 mL |
| 5 | 9.5 | 0.80 mL | 8.20 mL |
| 6 | 9.6 | 1.08 mL | 7.92 mL |
| 7 | 9.7 | 1.41 mL | 7.59 mL |
| 8 | 9.8 | 1.78 mL | 7.22 mL |
| 9 | 9.9 | 2.21 mL | 6.79 mL |
| 10 | 10.0 | 2.67 mL | 6.33 mL |
| 11-13 | 10.3 | 4.25 mL | 4.75 mL |
| 14-16 | 10.4 | 4.79 mL | 4.21 mL |
| 17-19 | 10.5 | 5.32 mL | 3.68 mL |
| 20-22 | 11.0 | 7.42 mL | 1.58 mL |
| 23-25 | 11.5 | 8.44 mL | 0.56 mL |

*The amount of 0.1M Na$_2$CO$_3$ in Table 1 does not include the approximate 0.5 milliliters of 0.1 molar sodium carbonate that was added with the 0.5 mL of 20 gram-per-liter solution of 2-[(1R,6R)-6-isopropenyl-3-methylcyclohex-2-en-1-yl]-3-hydroxy-5-pentylphenolate.

It was expected that 2-[(1R,6R)-6-isopropenyl-3-methylcyclohex-2-en-1-yl]-3-hydroxy-5-pentylphenolate would form 1R,6R CBD at pH's below a threshold pH as evidenced by an expected color change from purple (indicative of 2-[(1R,6R)-6-isopropenyl-3-methylcyclohex-2-en-1-yl]-3-hydroxy-5-pentylphenolate) to yellow-brown (indicative of 1R,6R CBD). No color change occurred at pH's of 9.1 and above. This finding suggested that either the pK$_a$ of 1R,6R CBD is less than 9.1, at least in dilute aqueous solutions, or that it may be possible to kinetically trap 2-[(1R,6R)-6-isopropenyl-3-methylcyclohex-2-en-1-yl]-3-hydroxy-5-pentylphenolate in an aqueous solution at a pH below the pK$_a$ of 1R,6R CBD.

Example 5. Determining the Approximate pK$_a$ of 1R,6R CBD 0.5 milliliters of the 20 gram-per-liter solution of 2-[(1R,6R)-6-isopropenyl-3-methylcyclohex-2-en-1-yl]-3-hydroxy-5-pentylphenolate described in Example 4 was diluted with 9.5 milliliters of distilled water comprising varying concentrations of sodium bicarbonate, and color was monitored as shown in Table 2. pH's were confirmed by multiple different measurements.

TABLE 2

Samples used to determine an approximate pK$_a$ for 1R,6R CBD

| Sample | pH | NaHCO$_3$ concentration (millimolar) | color |
|---|---|---|---|
| 26 | 8.0 | 1000 | faint purple |
| 27 | 8.3 | 500 | light purple |
| 28 | 8.6 | 250 | purple |
| 29 | 8.9 | 125 | purple |
| 30 | 9.2 | 62 | purple |

A color change was visually apparent at a pH of 8.0, and a subtle color change was visually apparent at a pH of 8.3. These findings suggest that the pK$_a$ of 1R,6R CBD was between 8.0 and 8.5 under the test conditions. This result is surprising given that previously reported pK$_a$'s for 1R,6R CBD range from 9.13 to 9.64 and because the chemically-related molecule resorcinol has a pK$_a$ of 9.15. Further, even though sample 26, which had a pH of 8.0, displayed a color change indicative of conversion from 2-[(1R,6R)-6-isopropenyl-3-methylcyclohex-2-en-1-yl]-3-hydroxy-5-pentylphenolate to 1R,6R CBD, no lipid phase formed, which suggests that the interconversion between 2-[(1R,6R)-6-isopropenyl-3-methylcyclohex-2-en-1-yl]-3-hydroxy-5-pentylphenolate and 1R,6R CBD in aqueous solution can kinetically trap 1R,6R CBD in the aqueous phase and inhibit the production of a lipid phase. These findings suggest that 2-[(1R,6R)-6-isopropenyl-3-methylcyclohex-2-en-1-yl]-3-hydroxy-5-pentylphenolate, the conjugate base of 1R,6R CBD, is suitable for use in beverages for human consumption.

Example 6. Confirming the Commercial Viability of Beverages Comprising 2-[(R,6R)-6-isopropenyl-3-methylcyclohex-2-en-1-yl]-3-hydroxy-5-pentylphenolate 20 milliliters of water was removed from a 1 liter bottle of ESSENTIA® OVERACHIEVING H$_2$O®. ESSENTIA® OVERACHIEVING H$_2$O® contains purified water, sodium bicarbonate, dipotassium phosphate, magnesium sulfate, and calcium chloride, and its pH was determined to be about 9.5. The 20 milliliters of removed water was replaced with 20 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce a sealed container comprising approximately 400 milligrams of 2-[(1R,6R)-6-isopropenyl-3-methylcyclohex-2-en-1-yl]-3-hydroxy-5-pentylphenolate. The pH of the liquid was measured and determined to be about 10. The liquid was purple and transparent.

5 milliliters of water was removed from a 500 milliliter bottle of DASANI® purified water. DASANI® purified water contains purified water, magnesium sulfate, potassium chloride, and sodium chloride, and its pH was determined to be about 7.0. The 5 milliliters of removed water was replaced with 5 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce a sealed container comprising approximately 100 milligrams of 2-[(1R,6R)-6-isopropenyl-3-methylcyclohex-2-en-1-yl]-3-hydroxy-5-pentylphenolate. The pH of the liquid was measured and determined to be about 9.5. The liquid was transparent and purple. The liquid had a faint flavor similar to the flavor of products comprising 1R,6R CBD in unflavored carriers.

0.5 milliliters of water was removed from a 500 milliliter bottle of DASANI® purified water. The 0.5 milliliters of removed water was replaced with 0.5 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce sealed container comprising approximately 10 milligrams of 2-[(1R,6R)-6-isopropenyl-3-methylcyclohex-2-en-1-yl]-3-hydroxy-5-pentylphenolate. The pH of the liquid was measured and determined to be about 8.5. The liquid was transparent and lacked discernable color.

The preceding experiments confirm that 2-[(1R,6R)-6-isopropenyl-3-methylcyclohex-2-en-1-yl]-3-hydroxy-5-pentylphenolate is suitable for use in beverages.

What is claimed is:
1. A composition, comprising:
   2-[(1R,6R)-6-isopropenyl-3-methylcyclohex-2-en-1-yl]-3-hydroxy-5-pentylphenolate at a concentration by weight of at least 5 parts per million and no greater than 25 percent;

2-[(1R,6R)-6-isopropenyl-3-methylcyclohex-2-en-1-yl]-5-pentylbenzene-1,3-diol;
water; and
potassium ion ($K^+$),
wherein:
the composition is a liquid; and
the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:10 and no greater than 1,000,000:1.

2. The composition of claim 1, comprising the 2-[(1R,6R)-6-isopropenyl-3-methylcyclohex-2-en-1-yl]-3-hydroxy-5-pentylphenolate at a concentration by weight of at least 5 percent and no greater than 25 percent.

3. The composition of claim 2, further comprising ethanol at a concentration by weight of at least 10 percent and no greater than 95 percent.

4. The composition of claim 3, comprising the water at a concentration by weight of at least 1 percent and no greater than 10 percent.

5. The composition of claim 4, comprising the potassium ion at a concentration of at least 10 millimoles per liter and no greater than 1 mole per liter.

6. The composition of claim 1, comprising the 2-[(1R,6R)-6-isopropenyl-3-methylcyclohex-2-en-1-yl]-3-hydroxy-5-pentylphenolate at a concentration by weight of at least 5 parts per million and no greater than 10 percent.

7. The composition of claim 6, further comprising ethanol at a concentration by weight of at least 10 percent by and no greater than 95 percent.

8. The composition of claim 6, further ethanol at a concentration by weight of at least 1 percent and no greater than 20 percent.

9. The composition of claim 6, further comprising ethanol at a concentration by weight of at least 10 parts per trillion and no greater than 0.5 percent.

10. The composition of claim 9, comprising the water at a concentration by weight of at least 50 percent and no greater than 99.999 percent, wherein the 2-[(1R,6R)-6-isopropenyl-3-methylcyclohex-2-en-1-yl]-3-hydroxy-5-pentylphenolate is dissolved in the water.

11. The composition of claim 10, comprising the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:1 and no greater than 10,000:1.

12. The composition of claim 11, wherein the composition has a pH of at least 8 and no greater than 12.

13. The composition of claim 12, further comprising one or more of sulfate ($SO_4^{2-}$), bicarbonate ($HCO_3^{1-}$), carbonate ($CO_3^{2-}$), phosphate ($PO_4^{3-}$), hydrogen phosphate ($HPO_4^{2-}$), hydrogen pyrophosphate ($HP_2O_7^{3-}$), hydrogen triphosphate ($HP_3O_{10}^{4-}$), and triphosphate ($P_3O_{10}^{5-}$).

14. The composition of claim 12, further comprising sodium ion ($Na^+$), wherein the composition comprises the potassium ion and the sodium ion at a combined concentration of at least 10 milligrams per liter and no greater than 1000 milligrams per liter.

15. The composition of claim 12, further comprising chloride ion ($Cl^{1-}$).

16. The composition of claim 12, further comprising calcium ion ($Ca^{2+}$).

17. The composition of claim 12, further comprising one or more of adenosylcobalamin, ascorbate, biotin, cyanocobalamin, folate, hydroxocobalamin, methylcobalamin, niacin, nicotinamide, pantothenate, pyridoxal, pyridoxamine, pyridoxine, riboflavin, thiamin, caffeine, theobromine, sucrose, fructose, glucose, acesulfame, saccharin, stevioside, rebaudioside A, sucralose, tagatose, erythritol, maltitol, xylitol, mannitol, isomalt, and a mogroside.

18. The composition of claim 17, comprising at least 5 milligrams and no greater than 500 milligrams of caffeine.

19. A liquid composition, comprising:
2-[(1R,6R)-6-isopropenyl-3-methylcyclohex-2-en-1-yl]-3-hydroxy-5-pentylphenolate at a concentration by weight of at least 5 percent and no greater than 25 percent;
2-[(1R,6R)-6-isopropenyl-3-methylcyclohex-2-en-1-yl]-5-pentylbenzene-1,3-diol, wherein the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:10 and no greater than 1,000,000:1;
ethanol at a concentration by weight of at least 10 percent and no greater than 95 percent;
water at a concentration by weight of at least 1 percent and no greater than 10 percent; and
potassium ion ($K^+$) at a concentration of at least 10 millimoles per liter and no greater than 1 mole per liter.

20. A liquid composition, comprising:
2-[(1R,6R)-6-isopropenyl-3-methylcyclohex-2-en-1-yl]-3-hydroxy-5-pentylphenolate at a concentration by weight of at least 5 parts per million and no greater than 10 percent;
2-[(1R,6R)-6-isopropenyl-3-methylcyclohex-2-en-1-yl]-5-pentylbenzene-1,3-diol, wherein the composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of at least 1:1 and no greater than 10,000:1;
water;
ethanol; and
potassium ion ($K^+$) and sodium ion ($Na^+$) at a combined concentration of at least 10 milligrams per liter and no greater than 1000 milligrams per liter.

* * * * *